US005679775A

United States Patent [19]

Boos et al.

[11] Patent Number: 5,679,775
[45] Date of Patent: Oct. 21, 1997

[54] PROCESS AND DEVICE FOR THE SIMULTANEOUS EXTRACORPOREAL ELIMINATION OF TUMOUR NECROSIS FACTOR AND BACTERIAL LIPOPOLYSACCHARIDES FROM WHOLE BLOOD AND/OR BLOOD PLASMA

[75] Inventors: Karl-Siegfried Boos, Gauting; Dietrich Seidel, Feldafing; Annette Trautwein, Hassloch; Gerold Morsch, Willinghausen, all of Germany

[73] Assignee: B. Braun Melsungen AG., Melsungen, Germany

[21] Appl. No.: 634,919

[22] Filed: Apr. 19, 1996

[30] Foreign Application Priority Data

Apr. 27, 1995 [DE] Germany ............... 195 15 554.8

[51] Int. Cl.$^6$ .................. C07K 3/12; C07K 3/20; C07K 13/00; A61M 1/34
[52] U.S. Cl. .................. 530/351; 530/382; 530/412; 530/415; 530/416; 530/417; 604/5; 604/6; 604/4; 436/86; 536/55.1; 536/123; 424/85.1
[58] Field of Search .................. 424/85.1; 436/86; 530/382, 412, 415, 416, 417; 536/55.1, 123; 604/4, 5, 6

[56] References Cited

U.S. PATENT DOCUMENTS

| 3,959,128 | 5/1976 | Harris | 210/692 |
|---|---|---|---|
| 4,213,859 | 7/1980 | Smakman et al. | 210/27 |
| 4,542,015 | 9/1985 | Smakman et al. | 424/79 |
| 4,576,928 | 3/1986 | Tani | 502/404 |
| 4,777,242 | 10/1988 | Nelles | 530/351 |
| 4,880,915 | 11/1989 | Kajihara | 530/413 |
| 4,923,439 | 5/1990 | Seidel et al. | 604/6 |
| 4,935,204 | 6/1990 | Seidel et al. | 424/101 |
| 5,055,447 | 10/1991 | Palladino et al. | 514/12 |
| 5,059,654 | 10/1991 | Hou | 525/54.1 |
| 5,108,596 | 4/1992 | Ookuma et al. | 210/198.2 |
| 5,178,864 | 1/1993 | Lees et al. | 424/94.1 |
| 5,252,216 | 10/1993 | Wasserman et al. | 210/635 |

FOREIGN PATENT DOCUMENTS

| 3110128 | 9/1982 | Germany. |
| 9209520 | 10/1992 | Rep. of Korea. |

OTHER PUBLICATIONS

Ruff, et al., Purification and Physico–Chemical Characterization of Rabbit Tumor Meciosis Factor, J. Immunol., 125(4), 1671–1677. 1980.

Hou, et al., Endotoxin Removal by Anion–Exchange Polymeric Matrix, Biotechnol. Appl. Biochem., 12(3), 315–324 1990.

Abbas, et al., Cellular and Molecular Immunology, 229–232. 1991.

The Merck Index Tenth Ed. "Polymyxin and Polymyxin B–Methanesulfonic Acid", p. 7448 (#'s 7445 and 7446). 1983.

Maini, R., Haemoperfusion Over Ion Exchange Resins and Polymeric Adsorbents, Journal of Articificial Organs, pp. 196–201. 1979.

*Primary Examiner*—Cecilia J. Tsang
*Assistant Examiner*—Jennifer Harle
*Attorney, Agent, or Firm*—Felfe & Lynch

[57] ABSTRACT

In order to remove tumor necrosis factor α (TNFα) or/and bacterial lipopolysaccharides (LPS, endotoxin) extracorporeally from whole blood or/and blood plasma in an extracorporeal perfusion system, the blood or plasma is passed over a cation exchanger and an anion exchanger material. A device according to the invention for the extracorporeal treatment of patient's blood or plasma therefore contains a cation exchanger material and an anion exchanger material wherein these materials are contained in at least one compartment of an extracorporeal perfusion system.

34 Claims, No Drawings

(1)

PROCESS AND DEVICE FOR THE SIMULTANEOUS EXTRACORPOREAL ELIMINATION OF TUMOUR NECROSIS FACTOR AND BACTERIAL LIPOPOLYSACCHARIDES FROM WHOLE BLOOD AND/OR BLOOD PLASMA

BACKGROUND OF THE INVENTION

The present invention concerns a process and a device for the simultaneous removal of tumour necrosis factor α (TNF α) and bacterial lipopolysaccharides (LPS) from whole blood or/and blood plasma in an extracorporeal perfusion system.

The selective and effective elimination of tumour necrosis factor α (TNF α) and of bacterial lipopolysaccharides (LPS, synonym: endotoxins) from the blood or plasma of patients is desirable from a medical point of view for the prevention and therapy of a gram-negative sepsis ("Intensivtherapie bei Sepsis und Multiorganversagen", Schuster, H. -P. ed., 1993, Springer Verlag, Berlin). The prognosis for a severe sepsis accompanied by shock is poor under the present standard therapy.

Septic shock is characterized by an abnormal distribution of the blood flow with a simultaneous drastic decrease in the peripheral resistance. In the acute phase there is a heart dilatation and the cardiac ejection fraction is significantly decreased. As the course of the disease progresses, two or more vital organ systems fail in rapid succession (multi-organ failure) as a clinical end point. Despite all therapeutic efforts, a lethal outcome must be expected in up to 50% of these intensive patients. The number of deaths caused by septic shock in the USA has been estimated to be ca. 100 000 per year (Parillo, J. E., "Septic Shock in Humans" in: Annals of Internal Medicine, Vol. 113, No. 3, 1990, 227–242).

Septic complications (shock, multi-organ failure) are caused by gram-positive and/or gram-negative bacteria. Invasion of the bacteria into the blood stream leads to secretion of exotoxins in the case of gram-positive bacteria (e.g. *Staphylococcus aureus*) and to release of LPS (endotoxins) from the outer bacterial cell wall when gram-negative bacteria (e.g. *Escherichia coli*) lyse. Bacterial lipopolysaccharides have a rod-like form and are composed of three structurally different regions. The carrier of the toxic properties is the lipid A. This substructure which is almost invariable for all lipopolysaccharides has a molecular weight of 2000 daltons and is composed of a phosphorylated D-glucosaminedisaccharide to which several long-chain fatty acids are linked in an ester or amide-like manner (Bacterial Endotoxic Lipopolysaccharides, Morrison, D. C., Ryan, J. L. eds., 1992, CRC Press).

LPS that has infiltrated into the blood stream binds to cells of the monocyte-macrophage system and stimulates these to an increased production and release of mediators (cytokines). Firstly tumour necrosis factor α is synthesized and secreted into the blood stream as an initial mediator and potent pro-inflammatory stimulus. The biologically active form of TNF α is composed of an aggregate of three identical polypeptide chains (157 amino acids, molecular weight: $17.4 \times 10^3$ daltons; Ziegler, E. J., N. Engl. J. Med. 318, 1988, 1533 ff.). The subsequent biological signal amplification by interleukins, leukotrienes, prostaglandins and interferons (mediator cascade) can eventually cause severe disturbances in the homeostasis of various biological control systems and organ systems such as for example the clinical picture of septic shock. Thus in many cases it has been shown that the clinical picture of sepsis correlates with the course and the level of the LPS concentration in the blood of the patients (Nitsche, D. et al., Intensive Care Med., 12 Suppl., 1986, 185 ff). Furthermore there are indications that there is a correlation between the TNF α concentration in blood plasma and the severity of septic shock and the later occurrence of death (Grau, G. E. et al., Immunol. Rev. 112, 1989, 49 ff.). Thus lipo-polysaccharides (LPS) as initiating toxins of gram-negative bacteria and TNF α as the initially released mediator play a key role with regard to the pathogenesis of a gram-negative sepsis.

The current therapy for sepsis comprises for example the administration of special antibiotics (Shenep, I. L., Morgan, K. A., J. Infect. Dis. 150, 1984, 380 ff.), of immunoglobulins (Schedel, F. et al., Crit. Care Med. 19, 1991, 1104 ff.) or of antibodies against LPS or TNF α (Werdan, K., Intensivmed. 30, 1993, 201 ff.) in addition to conventional measures of intensive therapy. However these treatment plans are also not able to significantly improve the prognosis (survival rate) of this high mortality patient group. In this connection first experimental studies in animals show that the simultaneous administration of antibodies against LPS and against TNF α can increase the survival rate (WO 91-01755).

However, antibody methods of therapy have serious deficiencies and disadvantages. The costs for the technically complicated isolation, purification and characterization of the appropriate antibodies are very high and there is a risk of an allergic counter-reaction (neutralizing immune response) of the body towards the antibodies. With regard to LPS antibodies the high rates of therapy failure are due among others to a too low specificity or affinity between the very heterogeneous LPS molecules and the monoclonal or polyclonal antibodies used. In this connection clinical studies in several centers had to be discontinued prematurely (Luce, J. M., Crit. Care Med. 21, 1993, 1233 ff).

A further procedure for neutralizing and eliminating pathogenic blood components is the treatment of whole blood or plasma in an extracorporeal perfusion system using appropriate and suitable adsorber materials. The following adsorber materials have been disclosed as being potentially suitable for the extracorporeal elimination of lipopolysaccharides (LPS, endotoxins) from whole blood and/or plasma: porous support materials with immobilized polymyxin B (U.S. Pat. No. 4,576,928; DE 3932 971). The clinical application of these affinity supports is very problematic since the ligand polymyxin B causes severe nephrotoxic and neurotoxic damage when released into the blood circulation.

The polyethylenimine-modified pearl celluloses disclosed in DE 41 13 602 A1 have a low binding capacity for LPS. If they were to be used in an extracorporeal perfusion system the medically tolerable extracorporeal dead volume would therefore be exceeded.

Polyanion-modified support materials are disclosed in DE 43 313 58 A1 for the extracorporeal adsorption apheresis of tumour necrosis factor α and/or LPS from whole blood and/or plasma. A disadvantage of these cation exchanger materials is that their selectivity and effectivity for LPS is too low and they only adsorb or eliminate ca. 30% of the lipopolysaccharides present in the perfused plasma. This is understandable since bacterial lipopolysaccharides are present as negatively charged molecules at a physiological pH value and thus have a low binding affinity for cation exchanger materials. However, as already described, in order to favorably influence the clinical course of the clinical picture of sepsis it is desirable from a pathophysiological and therapeutic point of view not only to remove both pathogenic blood components (LPS and TNF α) simultaneously from the circulation of the patient but also to accomplish this in a highly effective manner. This measure initially interrupts the biological mediator cascade and effectively abolishes the fatal synergistic effects of the two pathogens TNF α and LPS.

THE INVENTION

The object of the present invention is therefore to provide a process and a device for removing bacterial lipopolysaccharides (LPS) and tumour necrosis factor α (TNF α) simultaneously and highly effectively from whole blood or/and blood plasma in an extracorporeal perfusion system.

The following prerequisites must be fulfilled among others in order to be able to utilize such an elimination process (adsorption apheresis):

1) The pathogens should be eliminated as selectively and efficiently as possible.
2) The binding capacity of the adsorbents used should meet optimal practical requirements.
3) It must be possible to sterilize the adsorbents without loss or change in their properties with the aid of heat or gamma rays.
4) The adsorbents should allow an adequately high flow rate in the range up to 200 ml/min.
5) The elimination process must have the medically required biocompatibility and haemocompatibility and must not impair physiological control systems and protecting mechanisms such as for example the immune, complementary or coagulation system.

This object is achieved according to the invention by a process for the extracorporeal removal of tumour necrosis factor α (TNF α) or/and bacterial lipopolysaccharides (LPS, endotoxin) from whole blood or/and blood plasma in an extracorporeal perfusion system in which the blood or plasma is passed over a cation exchanger and an anion exchanger material.

Within the scope of the invention it is preferred in this connection to use cation exchanger and anion exchanger materials in a mixed form, namely as a mixed bed. In addition it is preferred that bifunctional ion exchanger materials be used i.e. materials which, due to the groups contained therein, are capable of binding anions as well as cations. Such materials and the production thereof are familiar to a person skilled in the art.

Within the scope of the present invention one preferably uses ion exchanger materials with support materials composed of porous glass or/and of silica gels coated with organic polymers or copolymers, cross-linked carbohydrates or/and organic polymers or copolymers in the form of porous particles or microporous membrane or/and hollow fibre structures.

A particularly suitable cation exchanger material according to the invention is composed of a support material to which functional groups made of synthetic or/and semisynthetic or/and natural polyanion chains are bound covalently and namely in a linear or branched form. If porous support materials are used their structure is preferably such that they have an average pore diameter of <30 nm or/and a molecular exclusion size for globular proteins of <$10^6$ and in particular <$2 \times 10^4$ daltons. The polyanion chains in this case in turn particularly preferably have an average molecular weight of 600 to $10^6$ daltons, in particular $5 \times 10^3$ to $5 \times 10^5$ daltons. Natural polyanion chains in the process according to the invention are preferably composed of biological polycarboxylic acids or/and polysulfonic acids and sulfated polysaccharides are particularly suitable.

Preferred synthetic or semisynthetic polyanion chains are polymers or copolymers of the monomers acrylic acid, methacrylic acid, vinylsulfonic acid, maleic acid; acrylic acid derivatives or/and methacrylic acid derivatives of the formula $H_2C=CR_1-CO-R_2$ in which the substituent $R_1$ is hydrogen or a methyl group and $R_2$ is a linear or/and branched chained aliphatic sulfonic acid, carboxylic acid or/and phosphoric acid group bound in an amide-like or ester-like manner; styrenesulfonic acid, anetholesulfonic acid, styrenephosphoric acid; glutamic acid, aspartic acid; adenosine-3',5'-diphosphate, guanosine-3',5'-diphosphate. Dextran sulfate cellulose is especially preferably used as the cation exchanger material within the scope of the present invention.

The anion exchangers used within the scope of the process according to the invention are preferably materials which contain cations or natural, synthetic or semisynthetic polycation chains as functional groups attached to support materials, in which the polycation chains can be present in a linear or branched form. Tertiary or/and quarternary amines are particularly preferably used as cation or polycation chains.

Preferred anion exchanger materials include in this case cross-linked or/and microgranular or/and microporous dialkylaminoalkyl, dialkylaminoaryl, trialkylammoniumalkyl or trialkylammoniumaryl celluloses or/and dialkylaminoalkyl, dialkylaminoaryl, trialkylammoniumalkyl or trialkylammoniumaryl-modified organic polymers or copolymers.

Surprisingly it was found within the scope of the present invention that anion exchangers according to the invention of which the heparin adsorber 500 (B. Braun Melsungen AG, Melsungen) is a particularly preferred example, adsorptively bind or eliminate bacterial lipopolysaccharides from whole blood or/and blood plasma at a physiological pH value (pH 7.4) with high selectivity and capacity (>3 mg LPS/g dry weight) (example 1).

The process according to the invention is preferably carried out at a physiological pH value.

In addition it was surprisingly found that such anion exchangers only adsorb a low amount of blood and plasma proteins which is harmless with regard to its composition even at a physiological pH value (example 3).

The invention in addition concerns a device for the extracorporeal treatment of patient blood or plasma which contains a cation exchanger and an anion exchanger material wherein these materials are contained in at least one compartment of an extracorporeal perfusion system. According to the invention two separate compartments or cartridges are present in the device one of which is filled with the anion exchanger material to remove LPS and the other of which is filled with the cation exchanger material to remove TNF α. The two compartments are then connected together via appropriate outlet and inlet openings such that the patient blood or plasma is passed uniformly through the two compartments. It is expedient to accomplish this with the aid of direct tube connections. Other types of connections are, however, also possible. In another preferred embodiment the anion and cation exchanger materials are present in a single compartment in the form of a mixed bed wherein the materials are mixed together and filled in a ratio that is appropriate for the practical requirements without impairing their advantageous properties or are present in the form of bivalent ion exchanger materials. This embodiment of the process according to the invention is particularly cost effective and simple and safe to handle especially since it also saves extracorporeal perfusion volume, and the connectors and components of the device which have to be sterilized and kept sterile can be kept to a low number.

Whole blood is either passed directly over the combined or mixed adsorber materials according to the invention with the aid of a peristaltic pump or it is first separated from cellular components over an appropriate separator (membrane filter, hollow fibre membrane, flow centrifuge). The plasma obtained in this manner is passed over the combined or mixed adsorber materials according to the invention, freed of the pathogens, subsequently combined with the cellular blood components and returned to the patient.

According to the invention it is therefore preferable that a plasma separation unit is connected in front of the compartment or compartments containing the ion exchanger materials of the device according to the invention. This plasma separation unit is preferably composed of a plasma fractionation filter which is impermeable to fibrinogen and/or low density lipoproteins (LDL).

The compartments of the device according to the invention which contain the ion exchanger materials are preferably each in the form of cylindrical housings the front ends of which are provided with caps which each have a central inlet and outlet connector. The housings preferably have a diameter of 3 to 20 cm, in particular 5 to 10 cm and a length of 1 to 40 cm, in particular 5 to 20 cm. Furthermore the housings are preferably made of glass or plastic and sieves are preferably integrated into the cap of the housings with a pore size of 10 to 200 µm and in particular 20 to 100 µm to eliminate particles. In addition it is preferred for the device according to the invention that the housings are integrated into a closed circuit in which the whole blood or blood plasma circulates by means of a pump.

The support materials for the cation and anion exchanger materials contained in the device according to the invention are preferably composed of porous glass or/and silica gel coated with organic polymers or copolymers, cross-linked carbohydrates or/and organic polymers or copolymers in the form of porous structures such as e.g. particles or microporous membrane or/and hollow fibre structures.

The cation exchanger material contained in the device according to the invention is preferably composed of a support material to which functional groups made of synthetic or/and semisynthetic or/and natural polyanion chains are bound covalently and namely in a linear or branched form. The polyanion chains of the cation exchanger preferably have an average molecular weight of 600 to $10^6$ daltons, in particular $5\times10^3$ to $5\times10^5$ daltons. If a porous support material is used the average pore diameter of the cation exchanger material according to the invention is preferably <30 nm or/and the molecular exclusion size for globular proteins is <$10^6$ and in particular <$2\times10^4$ daltons. In this connection it is preferred that natural polyanion chains of the cation exchanger material are composed of biological polycarboxylic acids or/and polysulfonic acids and particularly of sulfated polysaccharides and that synthetic or semisynthetic polyanion chains are polymers or copolymers of the monomers acrylic acid, methyacrylic acid, vinylsulfonic acid, maleic acid; acrylic acid derivatives or/and methacrylic acid derivatives of formula $H_2C=CR_1-CO-R_2$ in which the substituent $R_1$ is hydrogen or a methyl group and $R_2$ is a linear or/and branched-chained aliphatic sulfonic acid, carboxylic acid or/and phosphoric acid group bound in an amide-like or ester-like manner; styrenesulfonic acid, anetholesulfonic acid, styrenephosphoric acid; glutamic acid, aspartic acid; adenosine-3',5'-diphosphate, guanosine-3',5'-diphosphate.

The anion exchangers present in the device according to the invention are preferably materials which contain cations or natural, synthetic or semisynthetic polycation chains as functional groups attached to support materials, in which polycation chains can be present in a linear or branched form. Tertiary or/and quarternary amines are preferred as cation or as polycation chains.

A particularly preferred cation exchanger material is dextran sulfate cellulose and the anion exchanger material particularly preferably comprises cross-linked or/and microgranular or/and microporous dialkylaminoalkyl, dialkylaminoaryl, trialkylammoniumalkyl or trialkylammoniumaryl celluloses or/and dialkylaminoalkyl, dialkylaminoaryl, trialkylammoniumalkyl or trialkylammoniumaryl-modified organic polymers or copolymers.

The extracorporeal adsorption apheresis process according to the invention for the simultaneous elimination of LPS and TNF α have proven to be advantageous in that 1) the process is simple to monitor and safe to handle,
2) the extracorporeal dead volume is low,
3) the blood or blood plasma can be treated under physiological pH conditions,
4) when using the mixed bed adsorber the treated blood or blood plasma is exposed to a smaller foreign surface,
5) when using the mixed bed adsorber the amount of apparatus and tubing (disposable articles) is reduced and is thus more economic.

In summary the process according to the invention and the device according to the invention for the first time enable the two main mediators (bacterial lipopolysaccharides, tumour necrosis factor α) of septic disease states to be removed from the blood of patients under physiological pH conditions in a simple, selective and effective manner in a simply equipped extracorporeal perfusion system.

The present invention therefore also additionally concerns the use of a device according to the invention for the simultaneous extracorporeal removal of TNF α and LPS from patient's blood or plasma.

The invention is elucidated further by the following examples.

EXAMPLE 1

Device and Process for the Simultaneous Elimination of Lipopolysaccharide (LPS) and Tumour Necrosis Factor α (TNF α) from Human Plasma Experimental set-up A cartridge filled with the cation exchanger material according to the invention (bed volume: 160 ml, Liposorber™ LA-15, Kanegafuchi Chemical Industry, Osaka, Japan) was coupled via its outlet opening with the aid of a direct tubing connection to the inlet opening of a cartridge filled with the anion exchanger material according to the invention (bed volume: 500 ml; heparin adsorber 500, B. Braun Melsungen AG, Melsungen).

Experimental procedure

The two coupled adsorbers were firstly conditioned with 6 l of a pyrogen-free solution (Ringer solution composed of 140 mmol/l NaCl, 2 mmol/l $CaCl_2$ and 4 mmol/l KCl) (flow rate: 100/min). 1200 ml freshly collected human plasma was admixed under sterile conditions with 205 EU/ml (14.7 ng/ml) of bacterial lipopolysaccharide (*E. coli* 055: B 5 endotoxin, BioWhittaker Company, Walkersville, USA) and with 450 ng/ml tumour necrosis factor α (TNF α, Serva Co., Heidelberg).

Subsequently the human plasma was pumped with a peristaltic pump (flow rate: 30 ml/min) over the two adsorbers connected in series.

The quantitative determination of the lipopolysaccharide was carried out with the aid of chromogenic, kinetic Limulus-amoebocyte lysate (LAL) test (Chromogenix AB Co., Mölndal, Sweden). Tumour necrosis factor α was quantified using an EAISA (enzyme amplified sensitivity immunoassay; Medgenix Diagnostics SA Co., Fleurus, Belgium).

Experimental results:

The quantitative determination of LPS and TNF α in the human plasma perfused according to the invention showed that 70% of the added TNF α and 98% of the added LPS was eliminated by adsorption at a physiological pH value.

EXAMPLE 2

Adsorption and Elimination of Lipopolysaccharide (LPS, Endotoxin) from Human Plasma Under Physiological pH Conditions 1200 ml freshly collected human plasma was admixed with 205 EU/ml (14.7 ng/ml) of bacterial lipopolysaccharide (*E. coli* 055: B5 endotoxin, BioWhittaker Company, Walkersville, USA) and pumped at a flow rate of 30 ml/min over a heparin adsorber 500 (B. Braun Co., Melsungen) conditioned with 6000 ml of a pyrogen-free physiological saline solution. The quantitative determination of the lipopolysaccharide (chromogenic kinetic Limulus-amoebocyte lysate (LAL) test Chromogenix AB Co., Mölndal, Sweden) in the perfused eluate showed that 96% of the added lipopolysaccharide (endotoxin) was eliminated by binding to the adsorber.

EXAMPLE 3

Adsorption of Functional and Catalytic Plasma Proteins During the Perfusion of Human Plasma Under Physiological pH Conditions Over the Heparin Adsorber 500

After perfusion (flow rate: 30 ml/min) of 1000 ml freshly collected human plasma over a heparin adsorber 500 (B. Braun Co., Melsungen) conditioned with 6000 ml physiological saline solution, the adsorber cartridge is washed with 2000 ml of a physiological saline solution (flow rate: 30 ml/min). Subsequently the flow direction is reversed and the cartridge is washed for 30 minutes at a flow rate of 100 ml/min with 300 ml of a recirculating 2M sodium chloride solution in order to elute the plasma proteins bound by adsorption.

Table 1 shows that, after perfusion according to the invention of 1000 ml human plasma under physiological pH conditions over the heparin adsorber 500, only 3.1% of the total protein content of the untreated plasma was adsorptively bound.

The quantitative determination of the various plasma proteins—listed in table 1—show that only four proteins were eliminated to a significant extent. However, regarding these proteins (retinol binding protein, ceruloplasmin, prealbumin, IgM) it is known that an endogenous substitution occurs very rapidly and that a temporary reduction does not lead to any undesired physiological reactions.

The quantitative determination of the plasma enzymes GPT, GOT, AP, α-amylase, GT, GLDH, CK, LDH, CHE and lipase show that none of the examined enzymes is adsorptively bound and thereby eliminated.

TABLE 1

Adsorption of functional plasma proteins to the heparin adsorber 500 (B. Braun Co., Melsungen) at physiological pH value

|  | [mg]$^a$ | [%]$^b$ |
|---|---|---|
| Total protein | 2250 | 3.9 |
| Albumin | 750 | 2.1 |
| Prealbumin | 195 | 80.3 |
| IgA | 83 | 4.2 |
| IgG | 182 | 1.8 |
| IgM | 184 | 32.3 |
| Fibrinogen | 147 | 7.1 |
| $\beta_2$ microglobulin | 0.015 | 1.6 |
| $\alpha_2$ macroglobulin | 57 | 3.2 |
| Ceruloplasmin | 110 | 60.0 |
| Haptoglobin | 102 | 9.0 |
| Haemopexin | 50 | 7.4 |
| Retinol-binding protein | 24 | 64.9 |
| Ferritin | 0.002 | 6.9 |
| Transferrin | 94 | 5.2 |
| $\alpha_1$-antitrypsin | 58 | 3.9 |
| $\alpha_1$-glycoprotein | 50 | 9.1 |

$^a$relative to 1000 ml perfused human plasma
$^b$percentage relative to the value for untreated human plasma It will be understood that the specification and examples are illustrative but not limitative of the present invention and that other embodiments within the spirit and scope of the inventions will suggest themselves to those skilled in the art.

We claim:

1. A process for the extracorporeal removal of tumour necrosis factor α (TNFα) and/or bacterial lipopolysaccharides (LPS, endotoxin) from whole blood and/or blood plasma comprising: passing the whole blood and/or plasma over cation exchanger material and anion exchanger material.

2. The process of claim 1 wherein the cation exchanger material and the anion exchanger material are present as a mixed bed or as a bifunctional ion exchanger.

3. The process of claim 1 wherein the cation and/or anion exchanger material has a support material composed of porous glass and/or silica gel coated with an organic polymer or copolymer, cross-linked carbohydrate and/or organic polymer or copolymer in the form of porous particles or a microporous membrane and/or a hollow fiber structure.

4. The process of claim 1 wherein the cation exchanger material comprises a support material to which a linear or branched functional group of a synthetic and/or semi-synthetic and/or natural polyanion chain is covalently bound.

5. The process of claim 1 wherein the support material is porous with an average pore diameter of <30 nm and/or a molecular exclusion limit for globular proteins of <$10^6$ and preferably <$2 \times 10^4$ daltons.

6. The process of claim 4 wherein the polyanion chains has an average molecular weight of 600 to $10^6$ daltons and preferably $5 \times 10^3$ to $5 \times 10^5$ daltons.

7. The process of claim 4 wherein the natural polyanion chain is of a biological polycarboxylic and/or polysulfonic acid and preferably a sulfated polysaccharide.

8. The process of claim 4 wherein said synthetic and/or semi-synthetic polyanion chain comprise a polymer or copolymer of the monomers acrylic acid, methyacrylic acid, vinylsulfonic acid, maleic acid; acrylic acid derivatives and/or methacrylic acid derivatives of the formula $H_2C=CR_1—CO—R_2$ in which the substituent $R_1$ is hydrogen or a methyl group and $R_2$ is a linear and/or branched chained aliphatic sulfonic acid, carboxylic acid and/or phosphoric acid group bound in an amide-like or ester-like manner; styrenesulfonic acid, anetholesulfonic acid, styrenephosphoric acid; glutamic acid, aspartic acid; adenosine-3',5'-diphosphate, guanosine-3',5'-diphosphate.

9. The process of claim 1 wherein the cation exchanger material is dextran sulfate cellulose.

10. The process of claim 2 wherein the anion exchanger material contains cations or a natural, synthetic, or semi-synthetic polycation chain as a functional group attached to the support material, in which the polycation chain is present in a linear or branched form.

11. The process of claim 10 wherein the cations or polycations are tertiary and/or quarternary amines.

12. The process of claim 4 wherein the anion exchanger material is a cross-linked and/or microgranular and/or microporous dialkylaminoalkyl, dialkylaminoaryl, trialkylammoniumalkyl or trialkylammoniumaryl cellulose and/or dialkylaminoalkyl, dialkylaminoaryl, trialkylammoniumalkyl or trialkylammoniumaryl-modified organic polymer or copolymer.

13. The process of claim 1 wherein the process is conducted at a physiological pH value.

14. A device for the extracorporeal treatment of blood or plasma from a patient comprising: an extracorporeal perfusion system having at least one compartment containing a cation exchanger and an anion exchanger material.

15. The device of claim 14 wherein the anion exchanger and cation exchanger material are present in the least one compartment as a mixed bed or a bivalent ion exchanger.

16. The device of claim 14 wherein the device comprises at least two compartments, said least two compartments being connected to enable the blood or plasma to pass uniformly through both compartments and the anion exchanger and cation exchanger materials are each present in only one of the least two compartments.

17. The device of claim 14 further comprising a plasma separation unit connected to the least one compartment containing the exchanger material.

18. The device of claim 17 wherein the plasma separation unit comprises a plasma fractionation filter impermeable to fibrinogen and/or low density lipoproteins (LDL).

19. The device of claim 14 wherein the least one compartment comprises a cylindrical housing having a capped front end provided with an inlet and outlet.

20. The device of claim 19 wherein the housing has a diameter of 3 to 20 cm, preferably 5 to 10 cm, and a length of 1 to 40 cm, preferably 5 to 20 cm.

21. The device of claim 19 wherein the housing is of glass or plastic.

22. The device of claim 19 wherein the cap has a sieve with a pore size of 10 to 200 µm and preferably 20 to 100 µm to remove particles.

23. The device of claim 19 further comprising a circulating pump wherein the housing is integrated into a closed circuit and the pump circulates the whole blood and/or plasma.

24. The device of claim 14 wherein the cation exchanger material is composed of a support material to which a linear or branched functional group of a synthetic and/or semi-synthetic and/or natural polyanion chain is covalently bound.

25. The device of claim 24 wherein the polyanion chain of the cation exchanger material has an average molecular weight of 600 to $10^6$ daltons and preferably $5 \times 10^3$ to $5 \times 10^5$ daltons.

26. The device of claim 14 wherein the cation exchanger material has an average pore diameter of <30 nm and/or the molecular exclusion limit for globular proteins is <$10^6$ and preferably <$2 \times 10$ daltons.

27. The device of claim 24 wherein the natural polyanion chain of the cation exchanger material is composed of a biological polycarboxylic acid and/or polysulfonic acid and in particular a sulfated polysaccharide.

28. The device of claim 24 wherein the cation exchanger contains as the synthetic and/or semi-synthetic polyanion chain a polymer or copolymer of the monomers acrylic acid, methyacrylic acid, methyacrylic acid, vinylsulfonic acid, maleic acid; acrylic acid derivatives and/or methyacrylic acid derivatives of the formula $H_2C=Cr_1-CO-R_2$ in which the substituent $R_1$ is hydrogen or a methyl group and $R_2$ is linear and/or branched chained aliphatic sulfonic acid, carboxylic acid and/or phosphoric acid group bound in an amide-like or ester-like manner; styrenesulfonic acid, anetholesulfonic acid, styrenephosphoric acid, glutamic acid, aspartic acid; adenosine-3',5'-diphosphate, guanosine-3',5'-diphosphate.

29. The device of claim 14 wherein the anion exchanger material contains cations or a natural, synthetic, or semi-synthetic polycation chain as the functional group attached to the support material in which the polycation chain is present in a linear or branched form.

30. The device of claim 29 wherein the cation or polycation is a tertiary and/or quaternary amine.

31. The device of claim 14 wherein the cation and/or anion exchangers have support materials composed of porous glass and/or silica gel coated with an organic polymer or copolymer, cross-linked carbohydrate and/or organic polymer or copolymer in the form of porous particles or a microporous membrane and/or a hollow fiber structure.

32. The device of claim 14 wherein the cation exchanger material is dextran sulfate cellulose.

33. The device of claim 14 wherein the anion exchanger material comprises cross-linked and/or microgranular and/or microporous dialkylaminoalkyl, dialkylaminoaryl, trialkylammoniumalkyl or trialkylammoniumaryl cellulose and/or dialkylaminoalkyl-, dialkylaminoaryl-, trialkylammoniumalkyl- or trialkylammoniumaryl-modified organic polymer or copolymer.

34. A process for the simultaneous extracorporeal removal of TNF α and LPS from blood and/or plasma from a patient comprising: passing the blood or plasma from a patient through a device of claim 14.

* * * * *